United States Patent
Bier

(10) Patent No.: US 6,793,791 B2
(45) Date of Patent: Sep. 21, 2004

(54) VARIABLE-VOLUME DISPOSABLE ISOELECTRIC FOCUSING CELL AND METHOD OF ISOELECTRIC FOCUSING

(76) Inventor: Milan Bier, 4730 E. Placita Elegante, Tucson, AZ (US) 85718

( * ) Notice: Subject to any disclaimer, the term of this patent is extended or adjusted under 35 U.S.C. 154(b) by 0 days.

(21) Appl. No.: 10/374,943

(22) Filed: Feb. 26, 2003

(65) Prior Publication Data

US 2004/0163956 A1 Aug. 26, 2004

(51) Int. Cl.[7] ............... G01N 27/26; G01N 27/447; G01N 27/455; B01D 57/02
(52) U.S. Cl. ............... 204/548; 204/600; 204/644; 204/459; 204/610
(58) Field of Search ............... 204/450, 459, 204/548, 600, 610, 644

(56) References Cited

U.S. PATENT DOCUMENTS

| | | | | |
|---|---|---|---|---|
| 3,616,456 A | * | 10/1971 | Valmet | 204/644 |
| 3,915,839 A | * | 10/1975 | Rilbe et al. | 204/644 |
| 4,234,404 A | * | 11/1980 | Satoh | 204/644 |
| 4,401,538 A | * | 8/1983 | Hausfeld | 204/539 |
| 4,588,492 A | | 5/1986 | Bier | 204/301 |
| 4,897,169 A | | 1/1990 | Bier et al. | 204/183.2 |
| 5,173,164 A | * | 12/1992 | Egen et al. | 204/515 |
| 5,540,826 A | | 7/1996 | Bier et al. | 204/610 |

OTHER PUBLICATIONS

Baygents et al., "Recycling Electrophoretic Separations: Modeling of Isotachophoresis and Isoelectric Focusing," J. Chromatgr. A, 779:165–183, 1997.

* cited by examiner

*Primary Examiner*—Nam Nguyen
*Assistant Examiner*—Brian L Mutschler
(74) *Attorney, Agent, or Firm*—Antonio R. Durando; Quarles & Brady Streich Lang LLP

(57) ABSTRACT

An elastomeric cell is used as the disposable part of an apparatus for isoelectric focusing in free solution (without gels) in the 0.5 to 5 ml volume range. An inlet port is used for priming the cell and end-connectors for coupling with electrodes. A grid of parallel rods compresses the cell against a cold plate, thereby causing swelling of the skin of the cell between pairs of rods and forming contiguous fluid bubble-compartments for IEF separation. Before collection of separated fractions, the gap between the rods and the plate is further reduced so as to create distinct fluid compartments which now contain discrete products of separation. The separated fractions are collected by syringe-like devices by puncturing the elastomer skin. The plate, rods and deformable cell are capable of rotation or gentle rocking motion around the cell's main axis to avoid gravitational convection during the focusing process.

19 Claims, 6 Drawing Sheets

VARIABLE-VOLUME DISPOSABLE ISOELECTRIC FOCUSING CELL AND METHOD OF ISOELECTRIC FOCUSING

BACKGROUND OF THE INVENTION

1. Field of the Invention

This invention is related in general to electrophoretic apparatus and procedures for the separation and purification of biological materials. In particular, it pertains to a device for gel-free isoelectric focusing of fluids in relatively small and variable volumes.

2. Description of the Related Art

U.S. Pat. No. 4,897,169 (1990) taught that fluid stabilization can also be achieved by rapid recycling of process fluid through narrow channels formed between parallel flat plates. Another approach to fluid stabilization, disclosed in U.S. Pat. No. 4,588,492, consists of rotating the separation assembly around its horizontal axis. A commercial implementation of this concept, marketed by BIO-RAD Laboratories of Hercules, Calif., under the trademark ROTOFOR, received significant acceptance for scientific applications.

Nevertheless, there remained a need for instruments requiring smaller priming volumes, because available research quantities of protein solutions are often very small. A significant step toward that end was achieved by the invention described in U.S. Pat. No. 5,540,826 (1996). This disclosure taught that the multiple compartments of the instrument's cell need not be arranged in parallel, in filter-press like assemblies, but can be aligned in serpentine fashion, resembling somewhat cross-flow filtration. The patent taught streamlining of fluid flow using a narrow passage between adjacent cavities, or using a septum, such as a monofilament screen. In practice, though, implementation of these concepts proved to be functional but complicated (see Baygents et al., "Recycling Electrophoretic Separations: Modeling of Isotachophoresis and Isoelectric Focusing," J. Chromatogr. A, 779:165–183, 1997).

Therefore, there is still a need for simple devices that will separate by isoelectric focusing variable volumes of priming solution, say in the range of 0.5 to 5 ml. The present invention provides an easy and practical approach to accomplish these objectives while retaining the advantages achieved with prior-art instruments.

BRIEF SUMMARY OF THE INVENTION

In view of the foregoing, the present invention is intended to provide a device of simple construction for practicing isoelectric focusing of free solutions in variable volumes in the range of about 0.5–5 ml, an impossible task with prior art equipment. In addition, the invention is directed at a cell configuration that facilitates priming and collection of separated fractions without inter-compartmental mixing while retaining an effective cooling of the process fluid.

Therefore, according to one aspect of the invention, a deformable elastomer tube section, filled to the desired volume with free solution, is used as the focusing cell of an IEF unit. The tube is provided with a leak-proof inlet port for priming the cell with IEF fluid and with end electrode compartments or coupling means to connect the tube to external electrodes. One longitudinal side of the cell is placed in contact with a substantially horizontal cold plate that supports the cell and provides a heat sink to dissipate Joule heating generated by the electric field. The opposite longitudinal side of the cell is engaged by a plurality of transverse parallel rods impinging upon and increasingly pressing against the flexible surface of the cell. This compression causes a swelling of the skin of the cell between each pair of rods and forms distinct contiguous fluid-filled bubble-compartments for IEF separations. Fluid stabilization is achieved by means of control of the depth of gaps between contiguous bubbles. As isoelectric focusing progresses in conventional manner, the gap between the rods and the plate is progressively reduced in order to create separate contiguous fluid compartments which, at the end of the process, contain discrete products of separation. The plate, the rods and the deformable cell are assembled in a structure capable of rotation along the cell's horizontal axis to minimize gravitational convection within said compartments.

In the preferred procedure, at the assumed end of the IEF process the gaps between contiguous compartments in the focusing cell are closed completely by squeezing the transverse rods against the support plate. Thus, each bubble-compartment becomes isolated from adjacent ones. The contents of the bubbles can now be collected simultaneously or individually by puncturing the skin by means of hollow collection needles attached to syringes or tubing sections. A series of collection needles aligned with the compartments of the focusing cell can be used to simultaneously collect the contents of all compartments at the end of the focusing procedure.

According to yet another aspect of the invention, the focusing cell is manufactured with an expandable material, such as natural or synthetic rubber or silicone rubber, so that the total volume of free solution subjected to the IEF process may be varied and controlled by the priming step. In addition, cells of various diameters and length may be used with the same device to provide alternative ranges of volumes for IEF separation. The number of rods in the compression grid can be varied at will. Most likely, the grid will contain not less than 4 and not more than 19 rods, thus forming between 5 and 20 bubbles, respectively.

Various other purposes and advantages of the invention will become clear from its description in the specification that follows and from the novel features particularly pointed out in the appended claims. Therefore, for the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DESCRIPTION OF THE PREFERRED EMBODIMENTS OF THE INVENTION

The heart of this invention lies in the idea of using an expandable, elastomeric focusing cell to provide a variable-volume isoelectric focusing device. In addition, the deformable nature of the elastomer material of the cell makes it possible to isolate the products of separation into separate compartments of the cell to facilitate product collection free of mixing and contamination.

Figure 1:
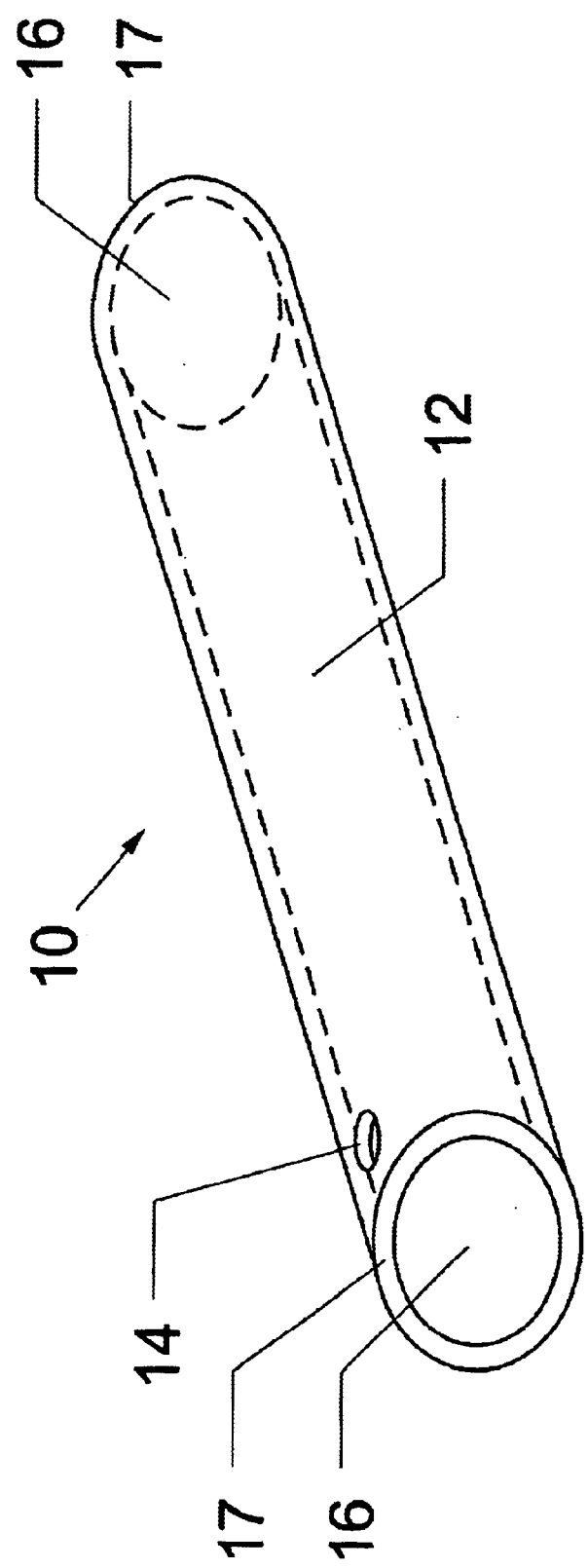
FIG. 1 is a perspective view of an exemplary focusing cell made with a tube section of elastomeric material according to the preferred embodiment of the invention.

Referring to the drawings, wherein the same numerals and symbols are used throughout to designate like parts, FIG. 1 illustrates in perspective view an exemplary focusing cell 10 according to the preferred embodiment of the invention. The cell 10 is shown as a flattened tube section 12 made of elastomeric material, preferably rubber latex or silicone rubber. In addition, any other natural or synthetic elastomer that is inert to the solution to be tested and is capable of expanding under internal pressure would be suitable to practice the invention. Besides natural rubber and silicone rubber, there is also a wide choice of synthetic rubbers, known under commercial names such as neoprene, nitrile rubber, polybutadiene, etc. The tube section 12 must also be provided with a leak-proof priming port 14, such as a membrane or valve that permits injection of the process solution but will not leak under internal pressure. Both ends of the tube are enclosed by semipermeable membranes 16, such as ion selective or dialyzing membranes, with coupling means 17 that permit electric coupling of the focusing cell 10 to conventional external electrodes and a DC power supply, not shown.

Figure 2:
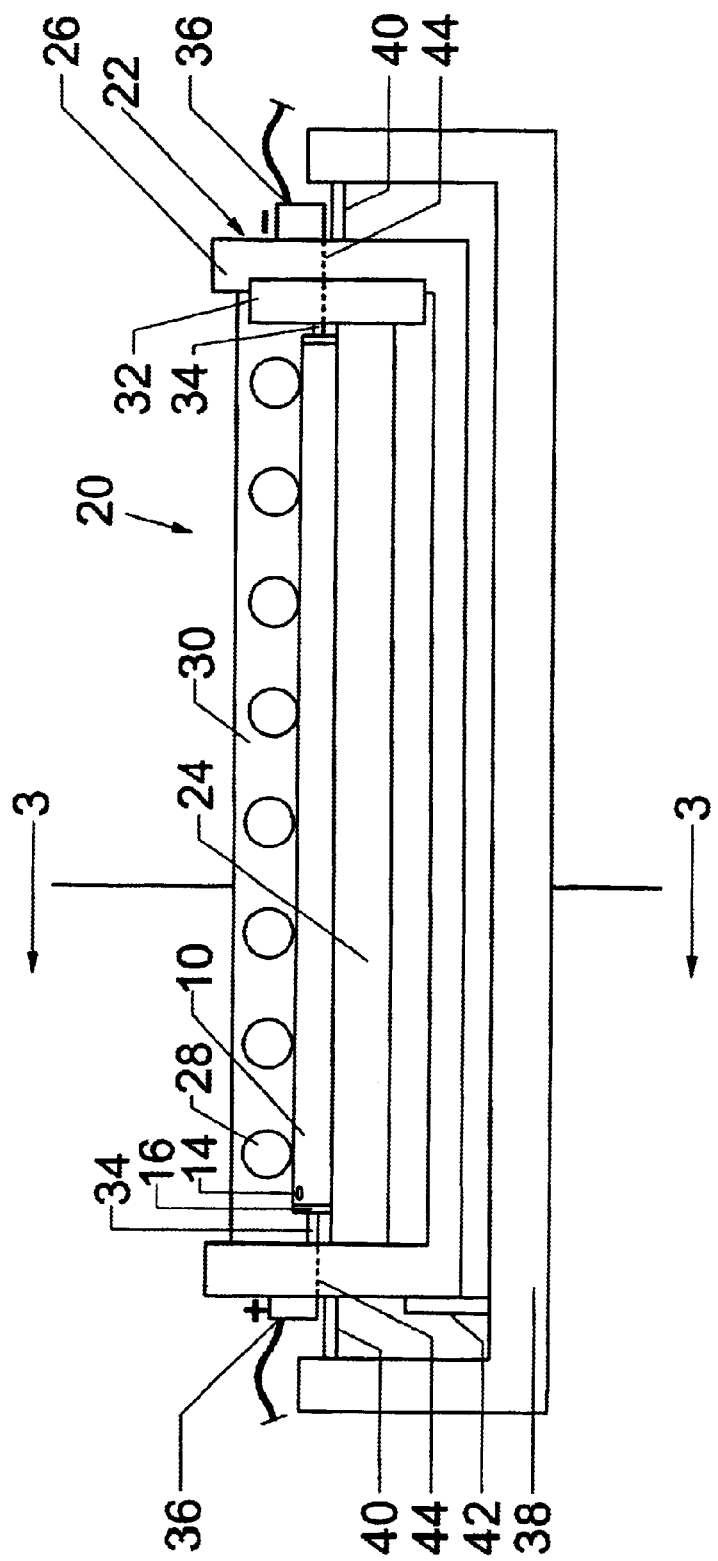
FIG. 2 is a schematic representation, in elevational view, of a variable-volume isoelectric focusing device according to the invention.
Figure 3:
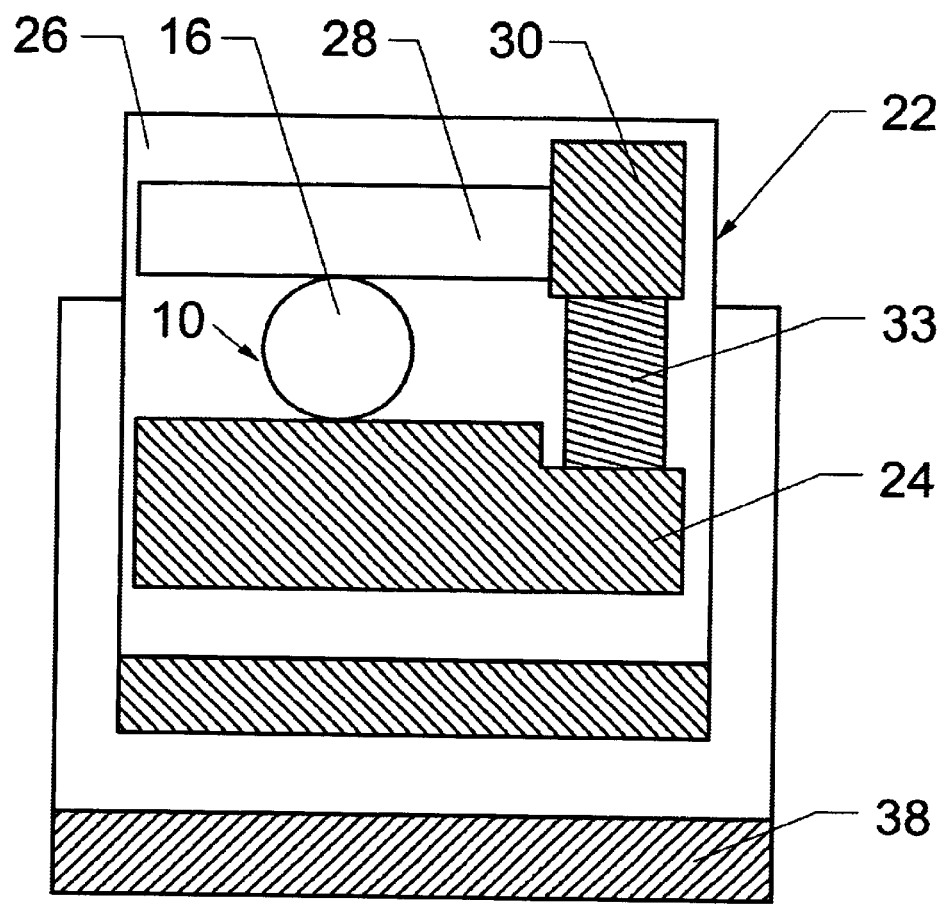
FIG. 3 is a schematic cross-section of the configuration of FIG. 2, as seen from line 3—3 in that figure.

As illustrated schematically in FIG. 2, the IEF device 20 of the invention includes a novel support assembly 22 for receiving and retaining the focusing cell 10 during the separation process. The assembly 22 comprises a substantially horizontal flat plate 24 mounted on a support structure 26 within the assembly 22. A plurality of parallel rods 28 is similarly mounted, by means of a frame 30, on the structure 26 opposite and transverse to the plate 24, so as to define an intermediate space for receiving the cell 10 of the invention. Preferably both, but at least one of the plate 24 or the frame 30 is slidably connected to the support structure 26 and is coupled to a mechanism 32 adapted to translate the plate and frame toward or away from one another, thereby varying the distance between the flat plate 24 and the rods 28. Said movement regulates the gap between successive bulging compartments of the elastomeric focusing cell. FIG. 3 illustrates schematically a cross-section of the configuration of FIG. 2, as seen from line 3—3 in that figure. A vertical travel guide 33 is shown to indicate schematically the ability to move the rod frame 30 or the plate 24 (or both) toward each other by the action of the mechanism 32.

The focusing cell is primed through the port 14, using a solution capable of generating pH gradients, as is well known in the art. Once filled, the focusing cell 10 is inserted between the flat plate 24 and the grid of rods 28 in a roughly horizontal orientation, and the cell's ends 16 are connected to two compartments 34 with electrodes that provide the DC potential necessary to carry out isoelectric focusing of the free solution contained in the cell 10. Each electrode compartment is connected to terminals of opposite polarity of a standard IEF power source (not shown) through appropriate electrical hardware and wiring 36. As well understood in the art, the plate 24 may be advantageously cooled in a number of ways, such as with a Peltier cooling unit or recirculating cold fluid. The assembly 22 is pivotally mounted on a frame 38 through a pair of axles 40 preferably aligned with the longitudinal axis of the cell 10, and a mechanism 42 is provided to either completely rotate the assembly or rock it over an arc covering about 180 degrees to avoid gravitationally induced convection due to density gradients arising during the IEF procedure.

The focusing cell 10 is filled with the desired volume of free solution to be processed and is mounted in the device 20, as illustrated in FIG. 2. Obviously, within the parameters of the dimensions of the various components of the assembly 22, different sizes may be selected for the cell's tube 12 to accommodate a range of capacities commensurate with the free-solution volumes required for various applications. After connection in conventional manner of the cell 10 to electrodes 44 in the compartments 34, the device is ready for operation according to standard IEF practice by applying a DC electric field across the two electrodes.

Figure 4:
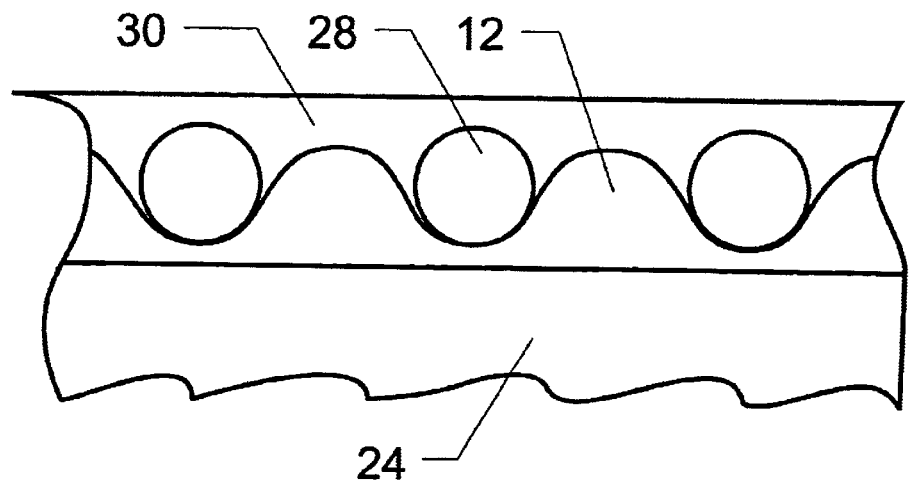
FIG. 4 is an enlarged partial view of the rods of the invention pressing against the elastomeric focusing cell to cause bulging between pairs of rods.

According to the invention, the distance between the cold plate 24 and the frame 30 supporting the grid of rods 28 is gradually reduced to compress the elastomer tube 12 and cause it to bulge in serpentine form between the rods, as illustrated in the partial view of FIG. 4. At the beginning of the focusing procedure, the grid of rods provides only a partial compression of the tube, thereby allowing migration of the materials subjected to fractionation along the length of the focusing cell 10. As isoelectric focusing progresses, the grid is made to further compress the cell progressively, in continuous or stepwise fashion, at the discretion of an operator or automatically according to a predetermined schedule suitable for the particular application. It is essential, however, that the gaps between successive bulges in the elastomeric tube 12 be nearly fully closed toward the end of the focusing procedure in order to provide best resolution, and be fully closed at the end of the focusing process to facilitate fraction collection. Throughout the process, the assembly 22 is rotated or gently rocked back and forth, preferably around the horizontal main axis of the cell 10, in order to prevent gravitational convection without causing fluid flow in the longitudinal direction.

Figure 5:
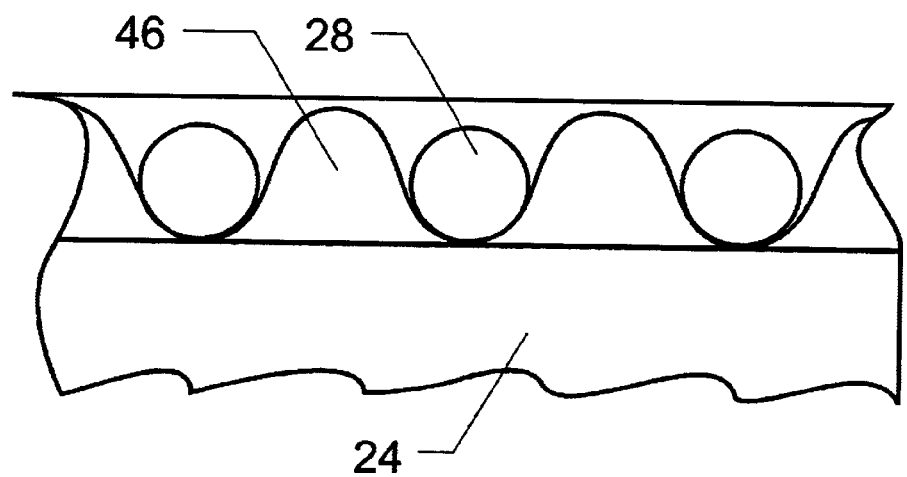
FIG. 5 is the view of FIG. 4 after the focusing cell of the invention has been pressed completely between the grid of rods and the supporting plate to produce separate compartments within the cell.
Figure 6:
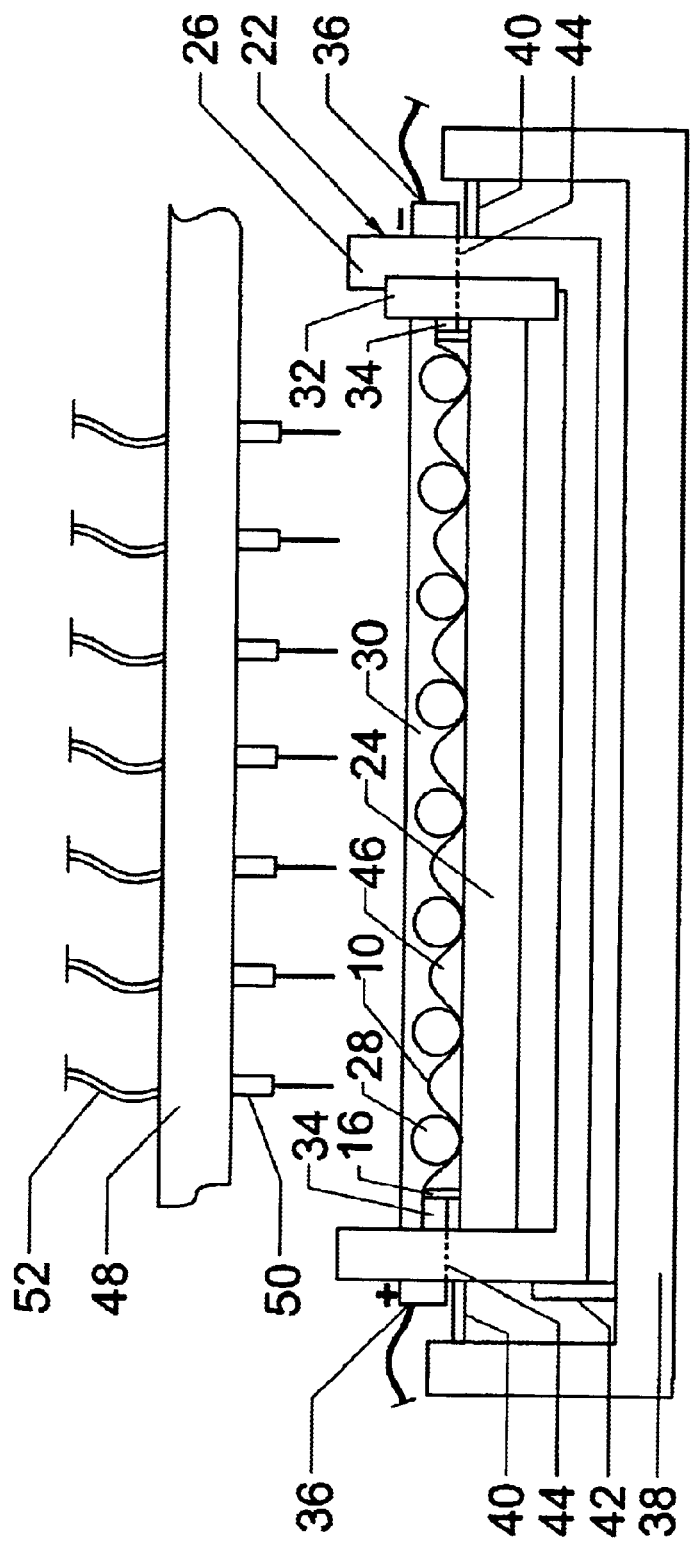
FIG. 6 is a view of the variable-volume isoelectric focusing device of FIG. 2 after full compression of the elastomeric cell, including an illustration of a bank of syringes for the collection of products from the separate cell compartments produced by the device.

When completion of the focusing procedure is assumed (based on elapsed time, visual observation, and/or decrease of the amperage, as normally done in the art), a final compression of the grid of rods 28 is carried out to fully segment the tube 12 into separated non-communicating bulge-compartments 46, as illustrated in FIG. 5, thereby segregating the IEF products focused in each segment. Thus, the contents of the compartments can be collected simply by puncturing them with sharp syringe-like needles, as known in the art. FIG. 6 illustrated the device 20 of the invention after full compression of the elastomeric cell and a bank 48 of syringe needles 50 with suitable fluid connections 52 provided to collect the products of IEF from each compartment 46.

It is noted that full compression of the rods 28 between segments of the focusing cell 10 and the corresponding complete segregation of each compartment 46 advantageously permits either simultaneous or sequential collection of individual volumes from the separate compartments.

Because of the total isolation of the solution volume in each compartment 46 from the rest of the cell, the withdrawal of fluid from one compartment and the corresponding pressure change occurring in that compartment does not cause fluid flow that might otherwise disturb the fractionated products in other compartments. As a result of the skin compression and inter-rod expansion of the elastomeric material of the focusing cell 10, the fluid tends to initially flow out of each compartment under its own internal pressure, but fluid collection is preferably also assisted by syringe vacuum or further compression of the ballooned sections of the cell. Inasmuch as the punctures of the focusing cell prevent its further use, it is contemplated that the elastomeric cell of the invention will be treated as a disposable component.

The invention shows that an expandable, deformable tube made of elastic material can be used advantageously to provide several degrees of flexibility of operation to IEF processes. The volumetric capacity of the uncompressed, tubular, elastomeric cell used for the invention can be easily calculated from its geometry. The volume capacity of each compartment after formation of separate compartments is similarly approximated as a fraction of the total priming volume initially delivered to the isoelectric focusing cell. As an example, a single bubble-compartment of spherical radius of 0.5 cm will contain approximately 0.26 ml of fluid. Assuming a grid assembly of 9 rods segmenting the focusing cell into 10 segments, the total priming volume will be about 2.6 ml. Depending on the full expansion capability of the elastomer, the actual capacity may be substantially greater or smaller. Thus, by varying the amount of free solution initially injected into the expandable cell, an operator is able to control the process volume to the desirable amount for a particular application. Moreover, elastomeric tubes 12 of different diameters may also be used to further vary the capacity of the apparatus of the invention, so long as the overall dimensions of the cell remain compatible for connection to the electrode compartments 34 and for engagement by the grid of rods 28. For example, it is expected that volumes as small as 0.5 ml, with a range up to 5 ml, can be processed with a single device 20 of the invention.

The invention has been described in terms of a grid of parallel, uniformly spaced-apart rods used for compressing the elastomeric cell of the invention. It is clear, though, that many modified configurations could be used within the scope of the invention. For example, the rods could be spaced in non-parallel fashion, or non-uniformly, at varied distances between different pairs of rods, in order to produce different-size compartments 46 to accommodate a particular distribution of products. Similarly, the invention is based broadly on the use of some means for squeezing the elastomeric cell to create separate compartments during the IEF procedure. Therefore, although the invention has been described in terms of round rods, any other structure capable of performing the function could be used in equivalent fashion. For example, round tubing, or either tubes or rods with a different cross-section (such as oval, square, or wedge-like), would be suitable.

Figure 7:
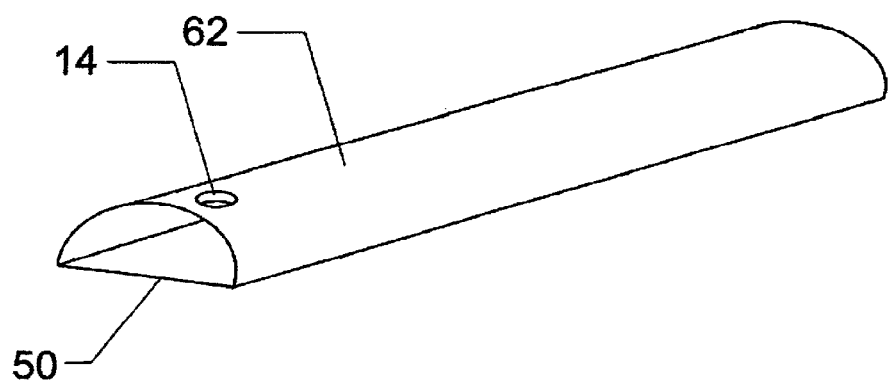
FIG. 7 is a view of an alternative embodiment of the focusing cell of the invention.

Several variants of the elastomeric cell can also be imagined within the concept of an expandable cell for IEF. For instance, rather than an elastomer tube, the cell could be made from an elongated elastic vessel of any sectional shape. Alternatively, as illustrated in FIG. 7, the cell could include a flat, relatively inelastic part 60 to be applied to the cold plate 24 and a frontal elastic part 62 to be compressed by the rod grid into serpentine configuration. The cold plate itself could be utilized to form a part of the cell by covering it with a sheet of elastomeric material and sealing the connecting edges. The IEF electrodes could also be incorporated within the cold plate or within the disposable cell 10. Similarly, if it is desired to separate electrode compartments from the focusing cell by means of semi-permeable or ion selective membranes, the membranes can be incorporated into the expandable cell, the cold-plate or the electrical connection of the power supply. It is also clearly understood in the art that all materials coming into contact with the fluid must be electrically non-conductive, such as rubber or plastics, with the exception of the actual electrodes.

Figure 8:
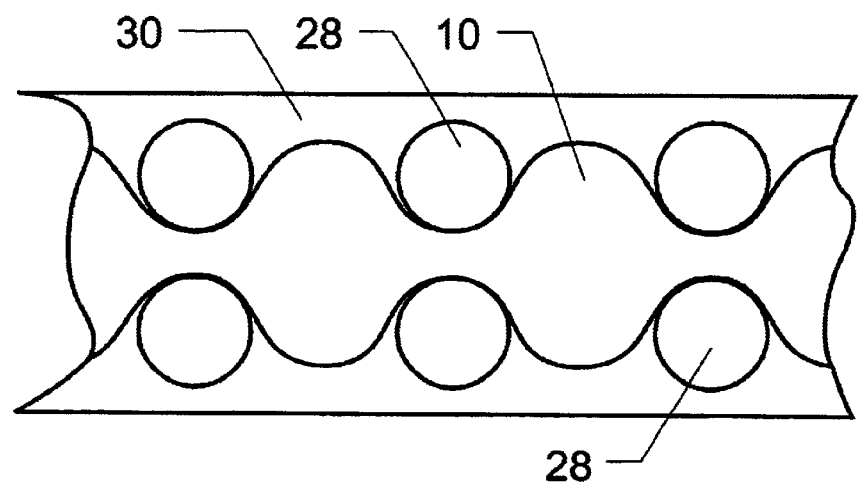
FIG. 8 is a partial schematic view of an alternative embodiment of the cell compression mechanism of the invention.

It is also recognized that the invention does not require that a flat plate, refrigerated or not, support the elastomeric IEF cell. For example, two sets of aligned transverse rods, adapted to progressively squeeze the elongated IEF cell into separate compartments could be used to practice the invention. In such a case, ballooning of the cell under compression could extend to both sides of the tube, as illustrated in partial view in FIG. 8. Also, the cell 10 could include a septum running the full length of the tube, such as a monofilament screen element of the type described in U.S. Pat. No. 5,540,826.

Various changes in the details, steps and components that have been described may be made by those skilled in the art within the principles and scope of the invention herein illustrated and defined in the appended claims. For example, other elastomeric materials could be used to manufacture the focusing cell, and additional structural configurations could be devised for the mechanism adopted to compress the cell and form separate compartments.

Thus, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products.

I claim:

1. An isoelectric focusing apparatus comprising:
   an elastomeric focusing cell connected to a pair of electrodes;
   a rigid structure supporting the cell; and
   means for compressing the cell against said structure to form contiguous multiple compartments within the cell;
   wherein said compressing means includes a grid of rods and a mechanism for pressing the cell between the rods and the rigid structure.

2. The apparatus of claim 1, wherein said rods are disposed in parallel to one another, are uniformly spaced, and are transverse to a longitudinal axis of the cell.

3. The apparatus of claim 1, wherein said rigid structure includes a plate.

4. The apparatus of claim 1, wherein said compressing means is operable to provide progressively increasing pressure on the cell during an isoelectric focusing procedure.

5. The apparatus of claim 1, further comprising a means for rotating the focusing cell around its longitudinal axis during an isoelectric focusing procedure.

6. The apparatus of claim 1, further comprising a means for rocking the focusing cell in a back-and-forth motion.

7. The apparatus of claim 1, further including means for collecting fluid from each of said multiple compartments of the focusing cell.

8. The apparatus of claim 7, wherein said collecting means includes a bank of syringes aligned with the multiple compartments of the focusing cell.

9. The apparatus of claim 3, wherein said plate incorporates a cooling means.

10. The apparatus of claim 1, wherein said rigid structure includes a cold plate; and wherein the device further comprises a means for rotating the focusing cell during the isoelectric focusing procedure and a means for collecting fluid from said multiple compartments of the focusing cell.

11. A method of improving segregation of fractionated products of isoelectric focusing, comprising the following steps:
   connecting an elastomeric focusing cell to a pair of isoelectric focusing electrodes;
   supporting the cell with a rigid structure;
   progressively compressing the cell against the rigid structure to form multiple contiguous compartments within the cell while performing an isoelectric focusing procedure; and,
   after completing said isoelectric focusing procedure, collecting fractions of said fractionated products from said multiple contiguous compartments.

12. The method of claim 11, further including the step of rotating the cell substantially about a longitudinal axis thereof during said isoelectric focusing procedure.

13. An isoelectric focusing apparatus comprising:
   a deformable focusing cell connected to a pair of electrodes;
   means for compressing said focusing cell to form contiguous bubble compartments within the cell;
   means for varying a degree to which said compressing means compresses the focusing cell, thereby progressively reducing fluidic communication between said contiguous bubble compartments.

14. The apparatus of claim 13, further comprising means for priming the deformable vessel with varying amounts of a free solution.

15. The apparatus of claim 13, wherein said contiguous bubble compartments are disposed in a linear substantially horizontal configuration.

16. The apparatus of claim 13, further comprising a means for rotating the focusing cell around its longitudinal axis during an isoelectric focusing procedure.

17. The apparatus of claim 13, further comprising a means for rocking the focusing cell in a back-and-forth motion.

18. The apparatus of claim 13, further including means for collecting fluid from each of said contiguous bubble compartments of the focusing cell.

19. The apparatus of claim 17, wherein said collecting means includes a bank of syringes aligned with the contiguous bubble compartments of the focusing cell.

* * * * *